United States Patent
Brown et al.

(10) Patent No.: US 11,998,102 B2
(45) Date of Patent: Jun. 4, 2024

(54) COMBINATION FLUID DISPENSER AND SCALP MASSAGER

(71) Applicant: Shameeka Brown, Brockton, MA (US)

(72) Inventors: Shameeka Brown, Brockton, MA (US); Eugene Harris, Brockton, MA (US)

(73) Assignee: Shameeka Brown, Brockton, MA (US)

( * ) Notice: Subject to any disclaimer, the term of this patent is extended or adjusted under 35 U.S.C. 154(b) by 708 days.

(21) Appl. No.: 17/248,639

(22) Filed: Feb. 1, 2021

(65) Prior Publication Data
US 2021/0361049 A1   Nov. 25, 2021

Related U.S. Application Data

(60) Provisional application No. 62/943,111, filed on Dec. 3, 2019.

(51) Int. Cl.
| | |
|---|---|
| *A61H 7/00* | (2006.01) |
| *A45D 34/04* | (2006.01) |
| *A45D 40/18* | (2006.01) |
| *A45D 40/26* | (2006.01) |

(52) U.S. Cl.
CPC ............. *A45D 40/18* (2013.01); *A45D 34/04* (2013.01); *A45D 40/26* (2013.01); *A61H 7/003* (2013.01); *A61H 2201/105* (2013.01); *A61H 2205/021* (2013.01)

(58) Field of Classification Search
CPC .......... A61N 5/0617; A61N 2005/0644; A61N 2005/0652; A61N 2005/0659; A61M 35/003; A61M 2210/06; A61H 2201/0153; A61H 2201/105; A61H 7/00; A61H 7/002; A61H 7/005; A61H 39/04; A61H 7/006; A61H 7/003; A61H 2205/021; A45D 34/042; A45D 40/18; A45D 34/04; A45D 34/00
See application file for complete search history.

(56) References Cited

U.S. PATENT DOCUMENTS

2014/0371690 A1* 12/2014 Sprada ................ B05B 11/103
604/311

FOREIGN PATENT DOCUMENTS

WO   WO-2010034802 A1 *   4/2010   ............. A61H 7/003

* cited by examiner

*Primary Examiner* — Margaret M Luarca
*Assistant Examiner* — Sarah B Lederer
(74) *Attorney, Agent, or Firm* — Wilmer Cutler Pickering Hale and Dorr LLP

(57) ABSTRACT

A scalp massager that simultaneously dispenses fluid is provided. A reservoir of fluid is fluidly coupled to a plurality of dispensing conduits, wherein each dispensing conduit is operatively associated with a resilient leg so that the outlet of the dispensing conduit is adjacent the distal end of the resilient leg. Both the resilient leg and the dispensing conduit each terminate at two adjacent points. The resilient leg may provide a foot that extends the two adjacent points for massaging the scalp.

11 Claims, 4 Drawing Sheets

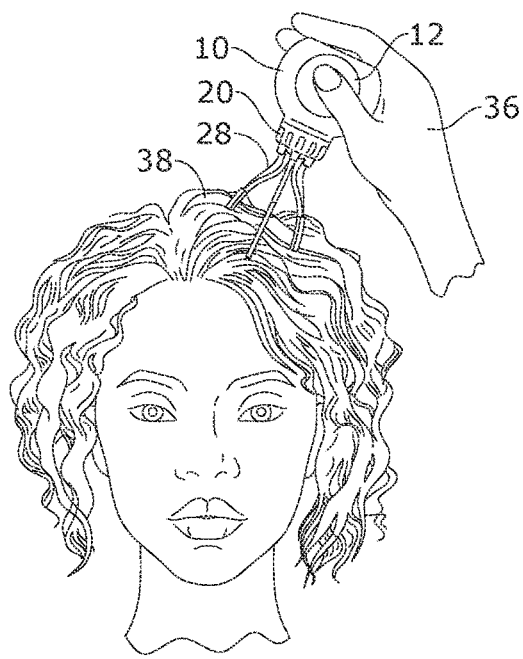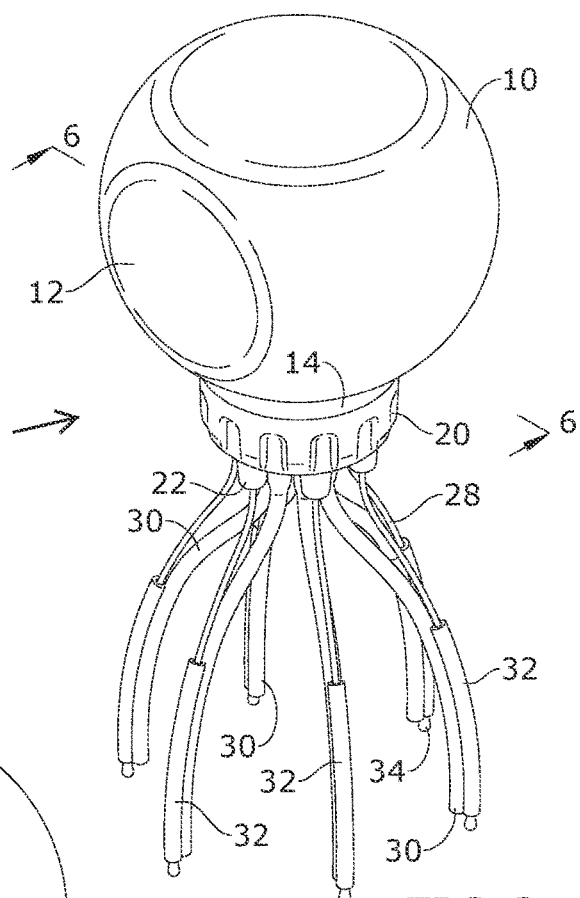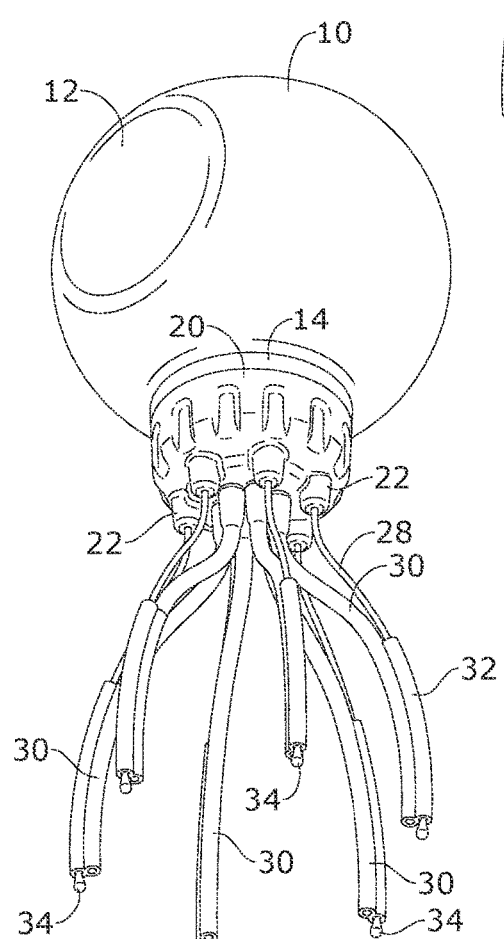
FIG.1
FIG.2
FIG.3

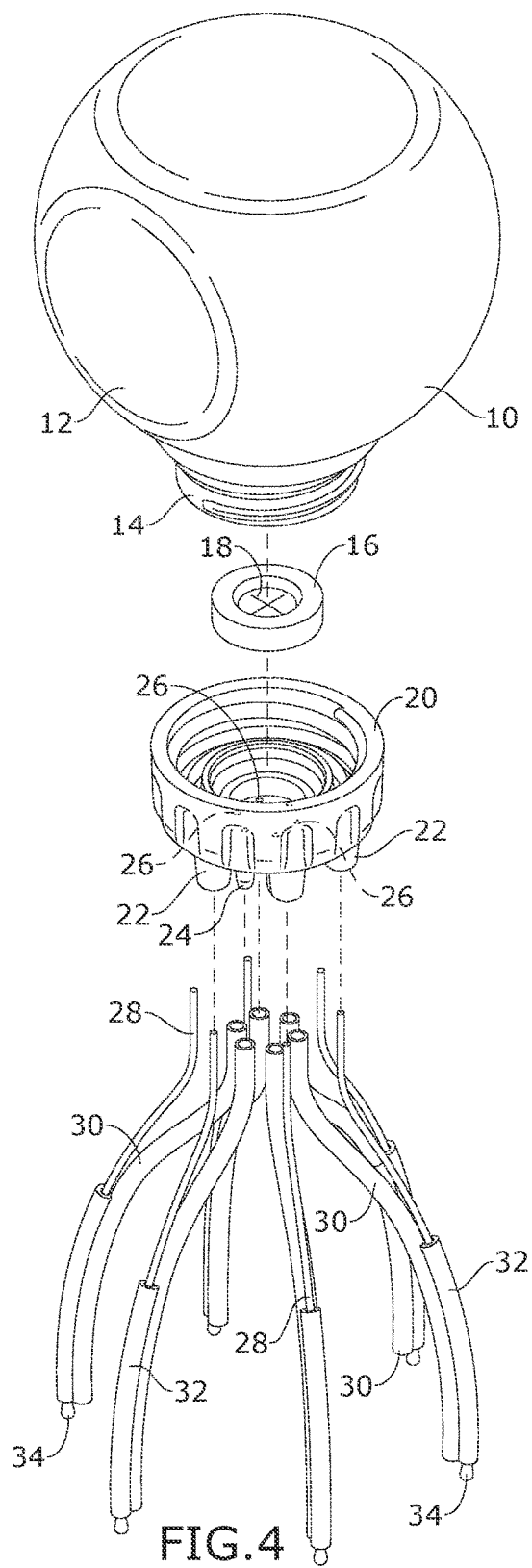
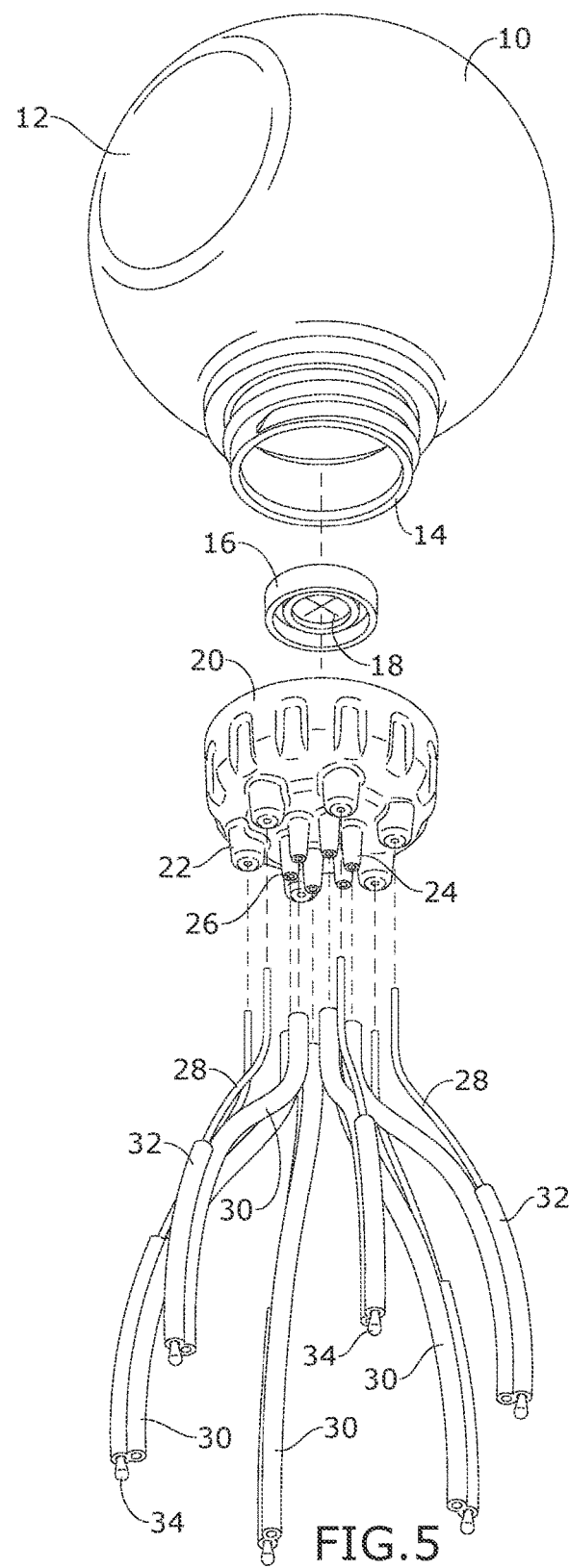

COMBINATION FLUID DISPENSER AND SCALP MASSAGER

CROSS-REFERENCE TO RELATED APPLICATION

This application claims the benefit of priority of U.S. provisional application No. 62/943,111 filed 3 Dec. 2020, the contents of which are herein incorporated by reference.

BACKGROUND OF THE INVENTION

The present invention relates to massagers and fluid dispensers and, more particularly, a combination fluid dispenser and scalp massager adapted to dispense fluid directly to the massaged scalp so as not to saturate the hair strands.

Dry scalp is a condition that plaques millions, if not billions, of people. Treatment for dry scalp includes the application of moisturizer through massage. Unfortunately, this is where the rubber meets the road, as currently the massager and the scalp moisturizer are not operatively associated—and so the moisturizer is applied prior to the separate massage—this tends to result in the oversaturation of the individual's hair. Hand massage may be very comfortable, but one person only has two hands, and the user still needs to dispense the moisturizer (e.g., spray oil, shampoo, or other liquid to the scalp) from time to time, thus requiring the one applying both to pause the massaging process to retrieve another bottle to spray on the scalp. While several massage devices are available to spray the fluid to the scalp, those devices cannot simultaneously provide a good massage and spray the fluid evenly around the scalp.

As can be seen, there is a need for a fluid dispenser that dispenses the fluid evenly through a plurality of spray extensions which facilitate a relevant massage, thereby simultaneously moisturizing the scalp without saturating hair with liquids. Each of the plurality of extensions coupled a resilient leg with a massaging tip and a dispensing conduit. This structure coupled the flexibility of the resilient leg to the spraying function of the dispensing conduit, allowing the user to manipulate the plurality of extensions to provide an even distribution of fluid with a good massage without any pause to retrieve a separate fluid dispenser.

SUMMARY OF THE INVENTION

In one aspect of the present invention, a device includes the following: a body defining a reservoir fluidly coupled to a manifold; a plurality of dispensing conduits extending from the manifold; and for each dispensing conduit, a resilient leg extends from the manifold spaced apart by a proximal distance from the dispensing conduit, wherein an outlet of the dispensing conduit is joined to a terminus of the resilient leg; a distal distance defined by the terminus and said outlet, wherein the proximal distance is at least twice the distal distance; a diaphragm between the body and the manifold; a foot extending from each terminus so as to entirely extend beyond said outlets, wherein the diaphragm comprises elastic sections defined by discontinuities in such a way as to be movable between a sealed condition and a fluid condition through pressure applied to the body, wherein the plurality of dispensing conduits defines a scalp receiving space having a scalp opening defined by said outlets, said scalp receiving space having a circumference greater than a circumference of said scalp opening, wherein the plurality of resilient legs is biased to apply pressure to an object engaging the scalp opening, whereby said object is massaged, wherein the plurality of resilient legs defines a second circumference greater than the circumference of the scalp receiving space, one or more grips along an exterior surface of the body, wherein the manifold provides a leg post for each resilient legs, wherein the manifold provides a conduit prong for each dispensing conduit, and wherein each leg post is spaced apart from each conduit prong.

In another aspect of the present invention, a method of massaging and moisturizing a scalp, the method including the following: joining a distal end of a resilient leg to an outlet of a dispensing conduit; and extending a plurality of resilient legs and a plurality of dispensing conduits from a manifold fluidly coupled to a handheld reservoir, wherein the manifold requires proximal ends of said resilient legs and dispensing conduits be spaced apart, wherein the plurality of dispensing conduits defines a scalp receiving space having a scalp opening defined by said outlets, said scalp receiving space having a circumference greater than a circumference of said scalp opening, wherein the plurality of resilient legs is biased to apply pressure to an object engaging the scalp opening; and massaging said object.

These and other features, aspects and advantages of the present invention will become better understood with reference to the following drawings, description and claims.

BRIEF DESCRIPTION OF THE DRAWINGS

FIG. 1 is a front perspective view of an exemplary embodiment of the present invention;

FIG. 2 is a top perspective view of an exemplary embodiment of the present invention;

FIG. 3 is a bottom perspective view of an exemplary embodiment of the present invention;

FIG. 4 is a top exploded perspective view of an exemplary embodiment of the present invention;

FIG. 5 is a bottom exploded perspective view of an exemplary embodiment of the present invention;

DETAILED DESCRIPTION OF THE INVENTION

Figure 6:
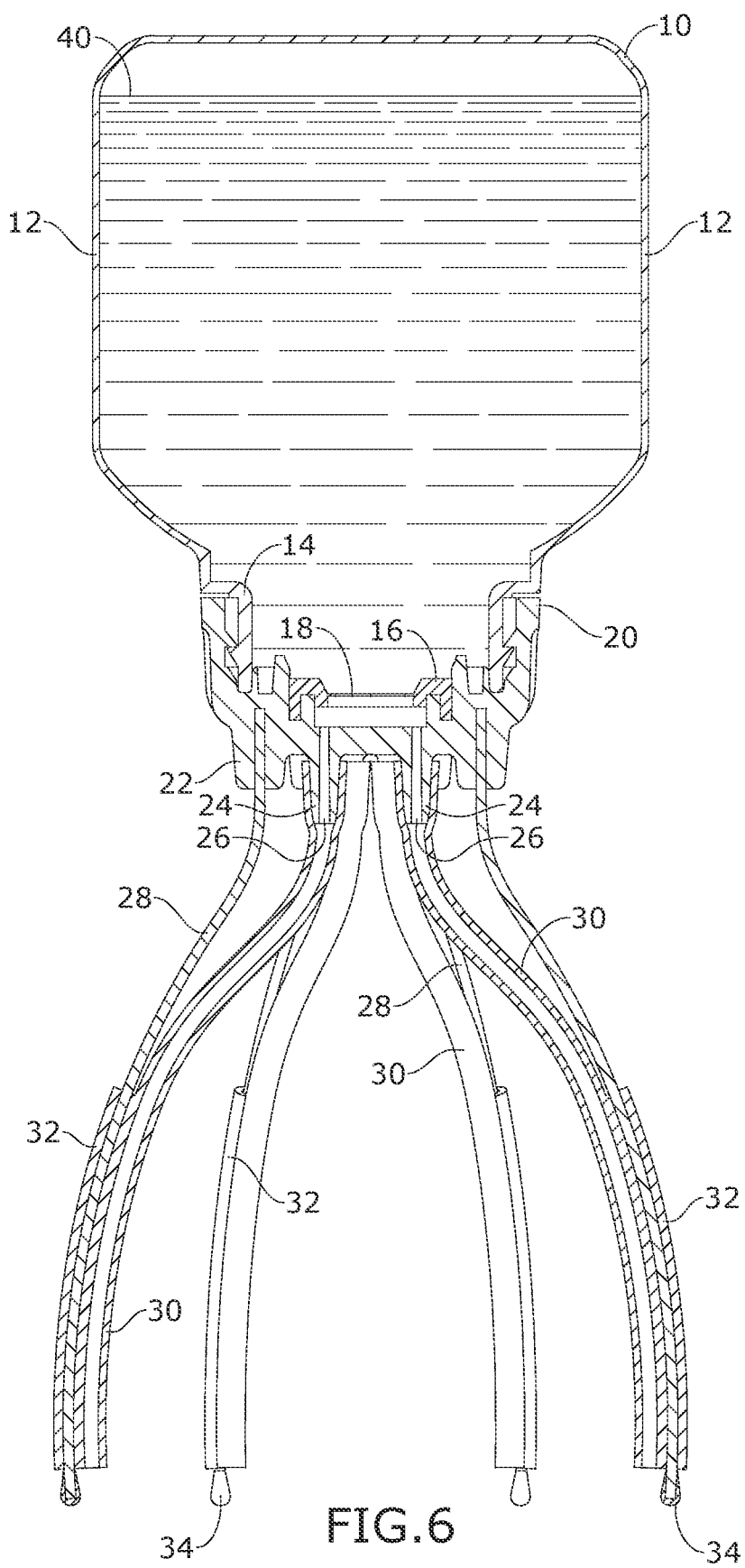
FIG. 6 is a section view of an exemplary embodiment of the present invention, taken along line 6-6 in FIG. 2.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a scalp massager that simultaneously dispenses fluid. A reservoir of fluid is fluidly coupled to a plurality of dispensing conduits, wherein each dispensing conduit is operatively associated with a resilient leg so that the outlet of the dispensing conduit is adjacent the distal end of the resilient leg. Both the resilient leg and the dispensing conduit each terminate at two adjacent points. The resilient leg may provide a foot that extends the two adjacent points for massaging the scalp.

Referring now to FIGS. 1 through 7, the present invention may include a combination fluid dispenser and scalp massager device 100 (hereafter, "dispenser massager device 100"). The dispenser massager device 100 may include a body 10 defining a reservoir fluidly coupled with a plurality of dispensing conduits 30, wherein each dispensing conduit 30 is operatively associated with a resilient leg 28 adapted to massage a scalp 38 or other parts of a living creature.

Fluidly coupling the reservoir and dispensing conduits 30 may be a manifold cap 20. The body 10 may have an opening defined by an opening periphery 14. In certain embodiments, the body 10 may be a bottle or bulbous hollow object, wherein the opening periphery 14 is a neck of that bottle. The body 10 may provide one or more grip/squeeze pads 12 for facilitating manually urging fluid 40 through said opening. A sealing ring 16 may be dimensioned and adapted to couple to the opening, wherein the sealing ring 16 provide a diaphragm and/or slit valve 18 sealing off the reservoir under non-urged conditions (i.e., where the body 10 is not under manual pressure or otherwise not being sufficiently urged, typically through pressure applied to the one or more grip/squeeze pads 12).

Figure 7:
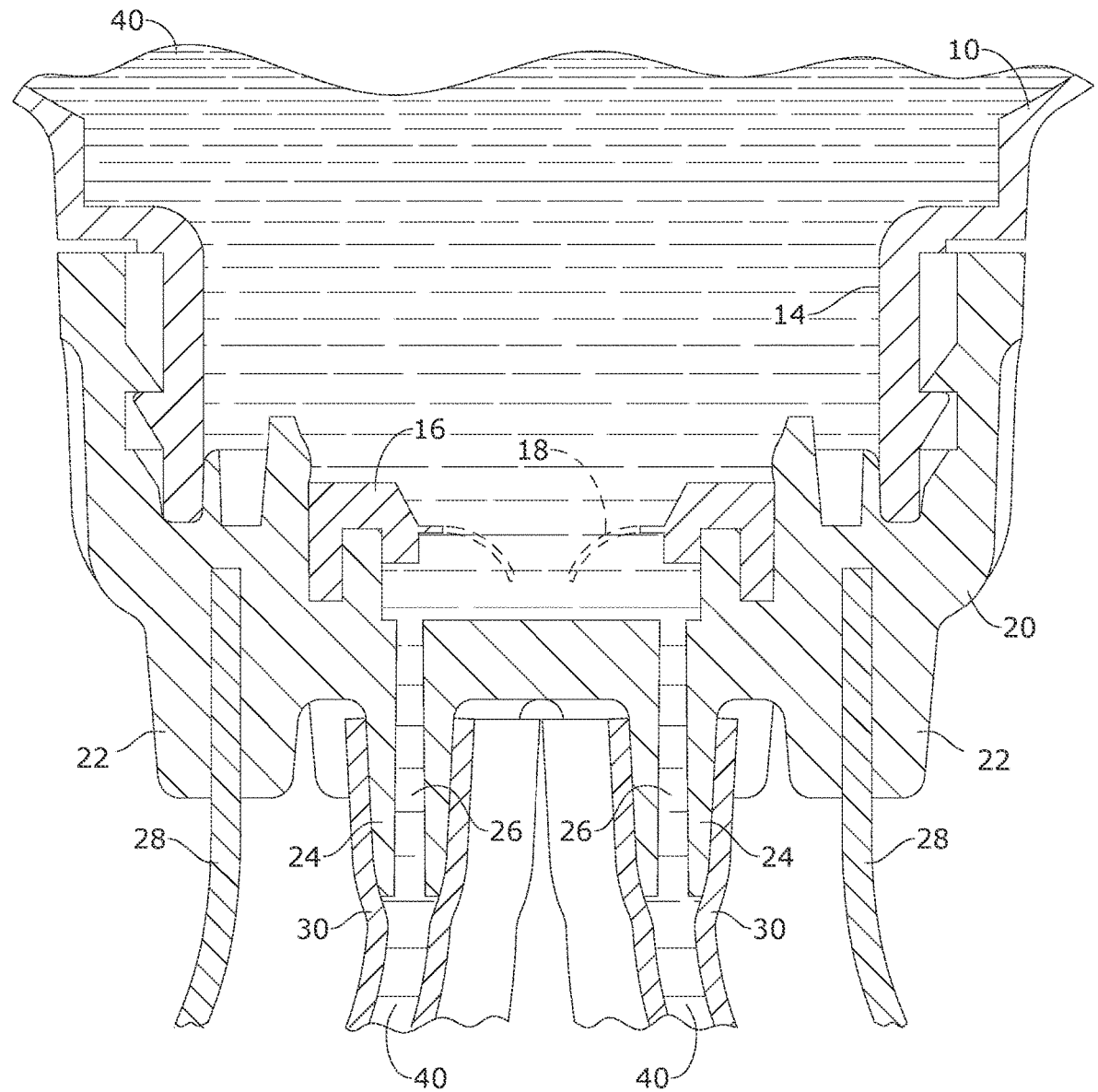
FIG. 7 is a detailed section view of FIG. 6, illustrating opening of diaphragm/slit valve 18 when the body 10 is urging fluid 10 to flow through the manifold conduit prongs 24 and the fluidly coupled dispensing tubes 30.

Referring to FIG. 7, the diaphragm and/or slit valve 18 may be elastic and defined by a plurality of sections (defined by discontinuities) that under an urged condition, elastically deform or bend in such a way that the fluid 40 in the reservoir is urged through the opening and into the manifold cap 20. The manifold cap 20 fluidly couples to the plurality of dispenser conduits 30 by way of manifold conduit prongs 24. Each conduit prong 24 defines a passageway 26 through which the fluid 40 may flow to a fluidly coupled dispenser conduit 30. Said fluidly coupling may be achieved by sliding a proximate end/inlet of the dispenser conduit 30 over the exterior of the conduit prong 24. The manifold cap 20 may also provide, separate from each conduit prongs 24, leg posts 22 that connect the resilient legs 28 to the manifold cap 20.

Referring to FIG. 6, each dispenser conduit 30 may operatively associate with a respective resilient leg 28 at a distal portion of both. In certain embodiments the operative association is achieved by way of a sleeve 32 provided by the dispenser conduit 30, wherein the resilient leg 29 is received through the sleeve 32. It being understood that other joining methods can be used so that the free ends of the dispenser conduit 30 and respective resilient leg 28 are joined so that their termini are adjacent to each other. Thus, each extension provides a resilient leg 28 coupled to a dispenser conduit 30 so that both end at share point, wherein each resilient leg 28 has a foot 34, which may be a smooth bulb or ball like structure to prevent scratching the scalp 38 of the user 36. Therefore, the foot 34 extends beyond the end of the dispensing conduit 30, which may be approximately one-sixteenth to one-quarter of an inch.

The body 10 may be made from rubber in the one embodiment, but other embodiments may use different materials. The body 10 is configured to allow the user to squeeze fluid 40 in its reservoir in the direction of the manifold cap 20 and increase the internal pressure of the body 10 and force the fluid 40 to flow through the manifold cap 20 and into the plurality of dispensing conduits 30 and onto the scalp 38 or other objects. The manifold cap 20 may also be configured as a second reservoir to allow the user 36 to introduce a second or more fluids into the flow. The manifold cap 20 is positioned between the body 10 and the plurality of dispensing conduits 30 and is configured to engulf the bottle and provide a base structure for the plurality of dispensing conduits 30. The manifold cap 20 further comprises a plurality of openings. Some of the plurality of openings traverse through the manifold cap 20 while others do not, depending on which component the opening is configured to hold.

In one embodiment, the bottle is made from silicone but other embodiments may use different materials. The bottle further comprises a plurality of openings. One opening comprises a cap for the user to introduce relevant liquid into the bottle while the rest of openings is configured to allow liquid to flow from the bottle into the plurality of extensions. A check valve may be positioned within the manifold cap 20 at the opposite end of the first half, the check valve may be configured to introduce air into the body to maintain a constant pressure within the body when the first half is not being pressed. This is to prevent liquid from reentering into the reservoir. In the one embodiment, the check valve is positioned in the distributor cap within the plurality of extensions, but other embodiments may change the check valve to different positions or allow the user to adjust the check valve accordingly.

The plurality of extensions may further comprise a tube, a wired leg, and a plurality of attaching mechanisms. The tube is made from silicone rubber in the one embodiment, but other embodiments may use different materials. The tube is connected to the cap by traversing through the opening of the second half. The tube is configured to allow the user to distribute liquid from the bottle to the scalp and further comprises a first end and a second end. The first end is connected to the cap. The second end is positioned on the opposite side of the first end and further comprises a slit valve. The slit valve is positioned on the inside of the cap on the second end and is configured to allow fluid to weep out when pressed, but also preventing air from entering the second end. The wired leg may be made from metal, but other embodiments may use different materials. The wired leg may further include a first end and a second end. The first end is connected to the second half by introducing the first end into one of the plurality of openings on the second half. The second end of the wired leg will be introduced into one of the plurality of tips to prevent the metallic second end from scratching the scalp. The wired leg may be connected to the second half but does not traverse through the wall of the second half. The wired leg is paired with the tube and is configured to create a flexible extension while allowing fluid flowed to the scalp.

A method of using the present invention may include the following. The dispenser massager device 100 disclosed above may be provided. A user 36 could gather the body 10, valved-manifold cap 20 with resilient legs 28 and dispensing conduits 30. The user could fill reservoir with a desired fluid 40 for moisturizing of a living being. The user 36 could screw the valved-manifold cap 20 with wired legs onto body 10. In certain embodiments, the user 36 may add a second fluid, mostly likely the more viscosity of the two fluids, into the space defined by the manifold cap 20, prior to operatively associating the manifold cap 20 and body 10.

The user 36 may apply pressure to an exterior of the body 10, possibly along the grip/squeeze pads 12, squeeze or otherwise urge the fluid 40 from the body 10, through the control valve 18 of the distribution cap 20 and through the dispensing conduit 30 coupled to each elongated, extending resilient leg 28, distributing the fluid 40 to the scalp 38, which is being massaged by the feet 34 of the resilient legs. The resilient leg 38 provides a flexible support for the dispensing conduit 30 which directs the fluid 40 to the scalp 38, and the rubber tip/foot 34 is used to provide massage to the scalp 38. The user 36 may move the body 10 in circular motion to effectuate a massage of the scalp 38 engaged by the feet 34. The user 36 can utilize liquid dispenser functionality without the massager functionality. An indicator to alert users to low liquid in bottle could be added.

It should be understood, of course, that the foregoing relates to exemplary embodiments of the invention and that modifications may be made without departing from the spirit and scope of the invention as set forth in the following claims.

What is claimed is:

1. A device comprising:
    a body defining a reservoir fluidly coupled to a manifold;
    a plurality of dispensing conduits extending from the manifold;
    for each dispensing conduit, a resilient leg extends from the manifold spaced apart by a proximal distance from the dispensing conduit, wherein an outlet of the dispensing conduit is joined to a terminus of the resilient leg; and
    a distal distance defined by the terminus and said outlet, wherein the proximal distance is at least twice the distal distance.

2. The device of claim 1, further comprising a diaphragm between the body and the manifold.

3. The device of claim 2, further comprising a foot extending from each terminus so as to entirely extend beyond said outlet.

4. The device of claim 3, wherein the diaphragm comprises elastic sections defined by discontinuities in such a way as to be movable between a sealed condition and a fluid condition through pressure applied to the body.

5. The device of claim 4, wherein the plurality of resilient legs is biased to apply pressure to an object, whereby said object is massaged.

6. The device of claim 5, further comprising one or more grips along an exterior surface of the body.

7. The device of claim 6, wherein the manifold provides a leg post for each resilient legs, wherein the manifold provides a conduit prong for each dispensing conduit, and wherein each leg post is spaced apart from each conduit prong.

8. A method of massaging and moisturizing a scalp, the method comprising:
    providing the device of claim 1;
    contacting an object's scalp with the termini of the resilient legs and/or the outlets of the dispensing conduits.

9. The method of claim 8, wherein the plurality of resilient legs is biased to apply pressure to the object's scalp.

10. The method of claim 9, further comprising massaging said object.

11. The method of claim 8, further comprising:
    providing a fluid in the body of the device; and
    applying pressure to the body to distribute the fluid to the subject's scalp through the dispensing conduits.

* * * * *